United States Patent [19]

Hindley et al.

[11] Patent Number: 4,692,465
[45] Date of Patent: Sep. 8, 1987

[54] 2-PHENYLETHYLAMINE DERIVATIVES

[75] Inventors: Richard M. Hindley, Reigate; John Berge, Redhill, both of England

[73] Assignee: Beecham Group PLC, Middlesex, England

[21] Appl. No.: 640,850

[22] Filed: Aug. 15, 1984

[30] Foreign Application Priority Data

Aug. 17, 1983 [GB] United Kingdom ............ 8322137
Dec. 22, 1983 [GB] United Kingdom ............ 8334293

[51] Int. Cl.$^4$ .................. A61K 31/24; C07C 101/30
[52] U.S. Cl. ............................ 514/539; 514/237;
514/320; 514/331; 514/422; 514/428; 514/469;
514/567; 514/620; 514/649; 514/651; 544/153;
544/162; 546/196; 546/232; 548/525; 548/569;
549/467; 560/42; 562/451; 564/165; 564/353;
564/354; 564/360
[58] Field of Search .................. 560/42, 45; 514/539,
514/237, 320, 331, 422, 428, 469, 567, 620, 651,
716, 649; 562/451; 564/165, 353, 354, 360;
549/467; 548/525, 569; 546/196, 232; 544/153,
162

[56] References Cited

U.S. PATENT DOCUMENTS

| | | | |
|---|---|---|---|
| 4,329,358 | 5/1982 | Ainsworth et al. | 560/42 |
| 4,338,333 | 7/1982 | Ainsworth et al. | 560/42 |
| 4,341,793 | 7/1982 | Ferris | 549/467 |
| 4,391,826 | 7/1983 | Mills et al. | 560/42 |
| 4,396,627 | 8/1983 | Ainsworth et al. | 560/42 |
| 4,629,737 | 12/1986 | Cantello | 560/42 |

FOREIGN PATENT DOCUMENTS 2084577 4/1982 United Kingdom ............ 549/467

OTHER PUBLICATIONS

McOmie, *Protective Groups in Organic Chemistry*, Plenum, London, (1973), pp. 95–103, 183–198.

*Primary Examiner*—Howard T. Mars
*Assistant Examiner*—Bruce D. Gray
*Attorney, Agent, or Firm*—Hopgood, Calimafde, Kalil, Blaustein & Judlowe

[57] ABSTRACT

Compounds of formula (I):

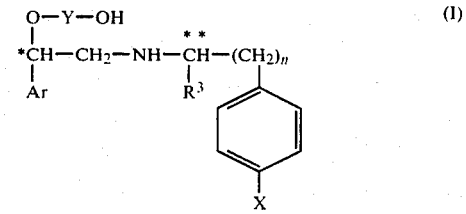

or a pharmaceutically acceptable salt, ester or amide thereof, wherein:
   Ar is benzofuran-2-yl, or phenyl optionally substituted by groups $R^1$ and/or $R^2$ wherein $R^1$ is halogen, trifluoromethyl or hydroxy and $R^2$ is halogen;
   $R^3$ is hydrogen or methyl;
   X is $-O(CH_2)_aCO_2H$, $-O(CH_2)bM$ or $-CO_2H$
in which
   a is an integer from 1 to 6,
   b is an integer from 2 to 7,
   M is hydroxy, $C_{1-6}$ alkoxy, phenyl $C_{1-6}$ alkoxy, or $-NR^4R^5$ in which $R^4$ and $R^5$ are each hydrogen or $C_{1-6}$ alkyl or together form a five or six membered heterocyclic ring;
   Y is $C_{2-6}$ straight or branched alkylene, with at least two carbon atoms between the $-O-$ and $-OH$;
and n is 1 or 2, having anti-obesity and/or anti-hyperglycaemic activity, processes for their preparation and their pharmaceutical use.

13 Claims, No Drawings

2-PHENYLETHYLAMINE DERIVATIVES

The present invention relates to derivatives of 2-phenylethylamine which have anti-obesity and/or anti-hyperglycaemic activity, to processes for their production and to their use in medicine.

EP No. 6766, EP No. 6735, EP No. 23385, EP No. 70133 and EP No. 70134 disclose derivatives of 2-phenylethylamine having anti-obesity and/or anti-hyperglycaemic activity.

A further group of compounds has now been discovered, which compounds have anti-obesity and/or anti-hyperglycaemic activity.

According to the present invention there is provided a compound of formula (I):

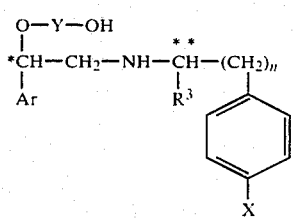

or a pharmaceutically acceptable salt, ester or amide thereof, wherein:

Ar is benzofuran-2-yl, or phenyl optionally substituted by groups $R^1$ and/or $R^2$ wherein $R^1$ is halogen, trifluoromethyl or hydroxy and $R^2$ is halogen;

$R^3$ is hydrogen or methyl;

X is $-O(CH_2)_aCO_2H$, $-O(CH_2)_bM$ or $-CO_2H$ in which a is an integer from 1 to 6, b is an integer from 2 to 7, M is hydroxy, $C_{1-6}$ alkoxy, phenyl $C_{1-6}$ alkoxy, or $-NR^4R^5$ in which $R^4$ and $R^5$ are each hydrogen or $C_{1-6}$ alkyl or together form a five or six membered heterocyclic ring;

Y is $C_{2-6}$ straight or branched alkylene, with at least two carbon atoms between the $-O-$ and $-OH$; and n is 1 or 2.

There is a group of compounds within formula (I) wherein Ar is phenyl optionally substituted by $R^1$ and $R^2$ which are halogen or trifluoromethyl and ortho-(or 2-)fluoro respectively and $R^3$, X, Y and n are as defined in formula (I).

There is a further group of compounds within formula (I) wherein Ar is phenyl optionally substituted by $R^1$ which is halogen or trifluoromethyl in the meta-(or 3-)position on the phenyl ring, and/or $R^2$ which is ortho-(or 2-)fluoro, X is $-O(CH_2)_aCO_2H$ or $-O(CH_2)_bM$ as defined and $R^3$, Y and n are as defined in formula (I).

When Ar is substituted phenyl, $R^1$ is preferably halogen in the meta-(or 3-)position on the aromatic ring. Preferably, $R^1$ is then chlorine. Preferably a is 1 and b is 2. Preferably n is 1.

Particularly preferred compounds are those wherein $R^3$ is methyl.

When M is $-NR^4R^5$, one of $R^4$ and $R^5$ is preferably hydrogen and the other is $C_{1-6}$ alkyl, preferably methyl or ethyl.

When $NR^4R^5$ together form a five or six membered heterocyclic ring, examples thereof include pyrrolidinyl, piperidinyl and morpholinyl.

Y is preferably ethylene or n-propylene.

Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicyclic acid or acetylsalicylic acid.

Preferred esters of the compounds of formula (I) are $C_{1-6}$ alkyl esters of the compounds wherein X is $-CO_2H$ or $-O(CH_2)_aCO_2H$. Particularly preferred esters are methyl and ethyl esters.

Preferred amides of the compounds of formula (I) are those wherein X is an amide of formula $-CONR^4R^5$ or $-O(CH_2)_aCONR^4R^5$, where $R^4$ and $R^5$ are as defined in formula (I).

When $R^3$ is methyl, the compounds of formula (I) have two asymmetric carbon atoms, marked with single and double asterisks in the formula. These compounds may, therefore, exist in four stereoisomeric forms. The present invention encompasses all stereoisomers of the compounds of formula (I) whether free from other stereoisomers or admixed with other stereoisomers in any proportion and thus includes, for instance, racemic mixtures of enantiomers.

Preferably the carbon atom marked with a single asterisk has the R configuration.

The most potent compounds of formula (I) are those wherein both asymmetric carbon atoms are in the R configuration. The absolute configuration of any compound of formula (I) may be determined by conventional X-ray crystallographic techniques.

The present invention also provides a process for producing a compound of formula (I), or a salt, ester or amide thereof, which process comprises reducing an oxo-group or a double bond of a compound of formula (II), or an ester or amide thereof:

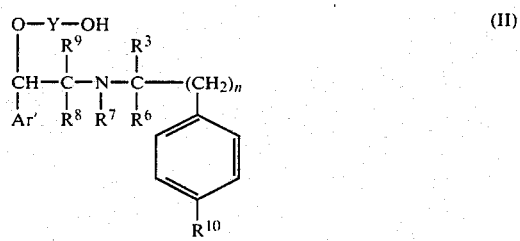

wherein:

$R^3$, Y and n are as defined in relation to formula (I);

Ar' is Ar as defined in formula (I) or a group convertible thereto;

$R^{10}$ is a group X as defined in relation to formula (I) or a group convertible to the group X;

$R^6$ is hydrogen or together with $R^7$ forms a bond;

$R^7$ is hydrogen or together with $R^6$ or $R^8$ forms a bond;

$R^8$ is hydrogen or together with $R^7$ forms a bond, or together with $R^9$ forms an oxo-group;

$R^9$ is hydrogen or together with $R^8$ forms an oxo-group, provided $R^6$ to $R^9$ are not all hydrogen when $R^{10}$ is X, and optionally thereafter converting a resulting compound wherein Ar' is other than Ar and/or $R^{10}$ is other than X to a compound of formula (I) and/or forming a salt of the compound of formula (I) so formed, and/or converting the compound of formula (I) so formed into a further compound of formula (I).

Where there are two reducible functional groups in the compound of formula (II) these may be reduced separately in any order or simultaneously.

The aforementioned reductions may be effected by conventional chemical or catalytic methods. Suitably, chemical reduction may be effected with lithium aluminium hydride, sodium cyanoborohydride, sodium borohydride or borane-methyl sulphide. Catalytic hydrogenation may be carried out using catalysts such as palladium on charcoal, or platinum, for instance, as reduced platinum oxide.

Reduction by sodium borohydride is conveniently effected in a lower alkanolic solvent such as methanol or ethanol. The reaction is generally carried out at from 0°–20° C.

Reduction by lithium aluminium hydride is conveniently effected in a dry, ether solvent such as diethyl ether or tetrahydrofuran at ambient or elevated temperatures.

Catalytic reduction is conveniently effected in a conventional hydrogenation solvent such as a lower alkanol, for instance ethanol. The hydrogenation is generally carried out under hydrogen gas at about 1 to 10 atmospheres pressure and at ambient or elevated temperatures.

Examples of Ar' when other than Ar include (when Ar is phenyl substituted by hydroxy), phenyl substituted by protected hydroxy. Suitable protecting groups are those which may be removed by conventional hydrogenolysis, such as benzyl.

Preferred aspects of the process of the invention comprise reducing a compound of formula (IIA):

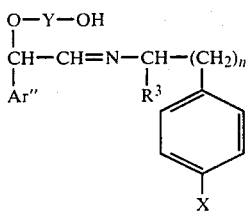

(IIA)

or reducing a compound of formula (IIB):

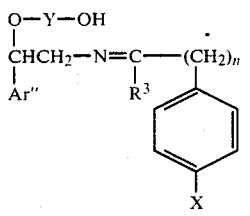

(IIB)

or reducing a compound of formula (IIC):

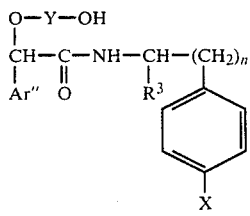

(IIC)

or reducing a compound of formula (IID):

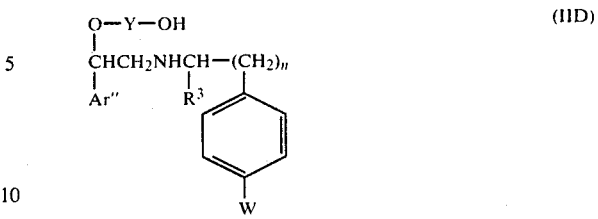

(IID)

wherein $R^3$, X, Y and n are as defined in relation to formula (II), Ar" is Ar or (when Ar in formula (I) is phenyl substituted by an $R^1$ hydroxy group) Ar substituted by protected hydroxy, and W is a group reducible to X, and thereafter optionally converting Ar" to Ar.

The present invention also provides a further process for producing a compound of formula (I), which comprises reacting an amine of formula (III):

$$A-NH_2 \qquad (III)$$

in which A represents a group of formula (IIIA) or (IIIB):

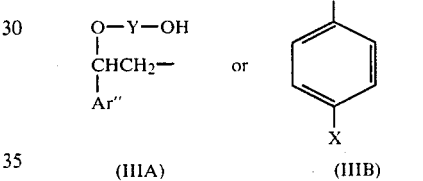

(IIIA)    (IIIB)

in which Ar", $R^3$, X, Y and n are as defined in relation to formulae (I) and (IIA-D)
with a compound of formula (IV):

$$B-Z \qquad (IV)$$

in which B represents a group of formula (IVA) or (IVB):

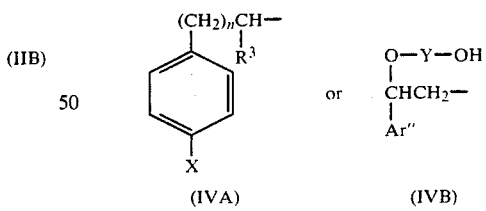

(IVA)    (IVB)

in which Ar", $R^3$, X, Y and n are as defined in relation to formula (I) and (IIA-D) and Z represents a leaving group, preferably halogen or a tosyloxy group, with the proviso that when A is a group of formula (IIIA), B is a group of formula (IVA) and when A is a group of formula (IIIB), B is a group of formula (IVB), and optionally thereafter converting Ar" to Ar, forming a salt of the compound of formula (I) so formed and/or converting the compound of formula (I) so formed into a further compound of formula (I).

The reaction of a compound of formula (III) with a compound of formula (IV) is conveniently carried out in a solvent, preferably dimethyl sulphoxide, at elevated temperature, preferably 50° C., for about two or three days.

The salts of compounds of formula (I) may be produced by treating the compound of formula (I) with the appropriate acid.

Compounds of formula (I) and salts thereof, produced by the above processes, may be recovered by conventional methods.

Compounds of formula (II) may themselves be produced by reacting an amine of formula (III) as hereinbefore defined, wherein A represents the moiety of formula:

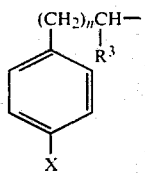

with a compound of formula (V):

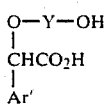

or reacting the amine of formula (III) wherein A represents the moiety of formula:

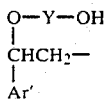

with a compound of formula (VI)

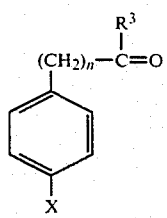

wherein Ar', R$^3$, X, Y and n are as defined in relation to formula (II).

Conventional conditions compatible with the particular compound of formula (V) or (VI) may be used for this reaction.

Thus, the reaction between compounds of formulae (III) wherein A is a group of formula (IIIA), and (VI) is conveniently conducted at elevated temperature under conditions resulting in the removal of the water formed during the reaction. A particularly suitable method is to perform the reaction in an inert solvent, such as benzene, under reflux and to remove the water azeotropically using a Dean and Stark trap.

The reaction between compounds of formulae (III) wherein A is a group of formula (IIIB), and (V) is conveniently conducted under standard peptide formation reaction conditions.

In the latter reaction, it may be desirable to protect the —OH group on Y in formula (V) with a conventional protecting group, such as acetate, and deprotect after the reaction.

It is often convenient to prepare the compound of formula (II) and reduce it, in situ, to the desired compound of formula (I) without isolation of the compound of formula (II).

By using single enantiomers of the compounds of formulae (III) and (V) a stereospecific synthesis of a compound of formula (IIC) is achieved. The compound of formula (IIC) may then be reduced to a compound of formula (I) without altering the configuration of the two asymmetric carbon atoms. Thus, for example, a compound of formula (III) with the R-absolute configuration and a compound of formula (V) with the R-absolute configuration would afford a compound of formula (IIC) and by subsequent reduction afford a compound of formula (I) with an R,R-absolute configuration.

A compound of formula (I) or a pharmaceutically acceptable salt, ester or amide thereof (hereinafter 'the drug') may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt, ester or amide thereof with a pharmaceutically acceptable carrier therefor.

As used herein the terms 'pharmaceutical composition' and 'pharmaceutically acceptable' embrace compositions and ingredients for both human and veterinary use.

Usually the compositions of the present invention will be adapted for oral administration although compositions for administration by other routes, such as by injection are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant or flavourant.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, and sucrose.

Most suitably the composition will be provided in unit dose form. Such unit doses will normally comprise 0.1 to 1000 mg of the drug, more usually 0.1 to 550 mg and favourably 0.1 to 250 mg.

The present invention further provides a method of treatment and/or prophylaxis of obesity in human or non-human animals, which method comprises administering an effective, non-toxic amount of a compound of formula (I) or a pharmaceutically acceptable salt, ester or amide thereof to the mammal.

The present invention further provides a method for the treatment and/or prophylaxis of hyperglycaemia in mammals including humans which method comprises administering an effective, non-toxic amount of a compound of formula (I) or a pharmaceutically acceptable salt, ester or amide thereof to the mammal.

Conveniently, the drug may be administered as a pharmaceutical composition as hereinbefore defined, and this forms a particular aspect of the present invention.

In treating hyperglycaemic or obese humans the drug may be taken in doses, such as those described above, one to six times a day in a manner such that the total daily dose for a 70 kg adult will generally be about 0.1 to 6000 mg, and more usually about 1 to 1500 mg. The more potent preferred compounds will generally be in unit doses containing 0.1 to 200 mg. Their daily dose will generally be about 0.5 to 500 mg, more usually 1 to 200 mg. In treating hyperglycaemic or obese animals, especially dogs, the drug may be administered by mouth, usually one or twice a day and at about 0.025 mg/kg to 25 mg/kg, for example 0.1 mg/kg to 20 mg/kg.

The invention will now be illustrated with reference to the following Examples.

In the Examples, the substituents in formula (I) are as shown in the following table.

| Ex | Ar | Y | $R_3$ | n | X | Salt |
|---|---|---|---|---|---|---|
| 1 | $3\text{-ClC}_6\text{H}_4-$ | $-(CH_2)_2-$ | $-CH_3$ | 1 | $-OCH_2CO_2CH_3$ | HCl |
| 2 | $3\text{-ClC}_6\text{H}_4-$ | $-(CH_2)_3-$ | $-CH_3$ | 1 | $-OCH_2CO_2CH_3$ | HCl |
| 3 | $3\text{-ClC}_6\text{H}_4-$ | $-(CH_2)_2-$ | $-CH_3$ | 1 | $-OCH_2CONHCH_3$ | HCl |
| 4 | $3\text{-ClC}_6\text{H}_4-$ | $-(CH_2)_2-$ | $-CH_3$ | 1 | $-OCH_2CH_2OH$ | HCl |
| 5 | $3\text{-ClC}_6\text{H}_4-$ | $-(CH_2)_2-$ | $-CH_3$ | 1 | $-OCH_2CH_2NHCH_3$ | di-HCl |
| 6 | $3\text{-CF}_3\text{C}_6\text{H}_4-$ | $-(CH_2)_2-$ | $-CH_3$ | 1 | $-OCH_2CO_2CH_3$ | HCl |
| 7 | $3\text{-Cl}-C_6\text{H}_4-$ | $-(CH_2)_2-$ | $-CH_3$ | 1 | $-CO_2CH_3$ | HCl |
| 8 | $C_6H_5-$ | $-(CH_2)_2-$ | $-CH_3$ | 1 | $-OCH_2CO_2CH_3$ | HCl |
| 9 | benzofuranyl | $-(CH_2)_2-$ | $-CH_3$ | 1 | $-OCH_2CO_2CH_3$ | HCl |
| 10 | $4\text{-HOC}_6\text{H}_4-$ | $-(CH_2)_2$ | $-CH_3$ | 1 | $-OCH_2CONH_2$ | — |
| 11 | $4\text{-HOC}_6\text{H}_4-$ | $-(CH_2)_2-$ | $-CH_3$ | 1 | $-OCH_2CO_2CH_3$ | HCl |

EXAMPLE 1

N-[2-(4-Carbomethoxymethoxyphenyl)-1-methylethyl]-2-(2-hyroxyethoxy)-2-(3-chlorophenyl)ethanamine hydrochloride 1-(4-Carbomethoxymethoxyphenyl)propan-2-one (4.4 g) and 2-(2-hydroxyethoxy)-2-(3-chlorophenyl)ethanamine (4.3 g) in methanol (100 ml) was hydrogenated in the presence of platinum (from platinum oxide, 50 mg) until hydrogen uptake ceased. The solution was filtered through diatomaceous earth, and the solvent removed under vacuum. Chromatography over silica gel in 2.5% methanol in dichloromethane gave an oil. Treatment of this oil with an ethereal solution of hydrogen chloride gave the title compound, mp 72°–75° C. (acetone-diethyl ether) as a 56:44 mixture of diastereoisomers.

$^1$H-nmr δ(DMSO-$d_6$): 1.20 (3H, d); 2.6–2.9 (1H, m); 3.0–3.8 (9H, complex m reduced to 8H with D$_2$O wash); 3.70 (3H, s); 4.78 (2H, s); 4.9–5.2 (1H, m); 6.90 (2H, d); 7.24 (2H, d); 7.3–7.6 (4H, m); 9.0–9.5 (1H, brd m, exchanges with D$_2$O); 9.6–10.2 (1H, brd m, exchanges with D$_2$O).

EXAMPLE 2

N-[2-(4-Carbomethoxymethoxyphenyl)-1-methylethyl]-2-(3-hydroxypropoxy)-2-(3-chlorophenyl)ethanamine hydrochloride The title compound was prepared as a 56:44 mixture of diastereoisomers, mp 110°–114° C. (ethyl acetate-cyclohexane), from 1-(4-carbomethoxymethoxyphenyl)propan-2-one (4.3 g) and 2-(3-hydroxypropoxy)-2-(3-chlorophenyl)ethanamine (4.5 g) by an analogous procedure to that described in Example 1.

$^1$H-nmr δ(DMSO-$d_6$): 1.0–1.3 (3H, m); 1.5–1.9 (2H, m); 2.6–2.9 (1H, m); 3.0–3.8 (8H, complex m); 3.70 (3H, s); 4.5–4.8 (1H, brd m, exchanges with D$_2$O) 4.78 (2H, s); 4.8–5.1 (1H, m); 6.90 (2H, d); 7.21 (2H, d); 7.3–7.6 (4H, m); 8.8–9.3 (1H, brd m, exchanges with D$_2$O); 9.8–10.3 (1H, brd m, exchanges with D$_2$O).

EXAMPLE 3

N-[2-(4-Methylaminocarbonylmethoxyphenyl)-1-methylethyl]-2-(2-hydroxyethoxy)-2-(3-chlorophenyl)ethanamine hydrochloride A mixture of N-[2-(4-carbomethoxymethoxyphenyl)-1-methylethyl]-2-(2-hydroxyethoxy)-2-(3-chlorophenyl)ethanamine (4.0 g) and 33% methylamine in ethanol (50 ml) was heated under reflux for 1.5 h. The mixture was evaporated under reduced pressure and the residue converted to its hydrochloride by addition of ethereal hydrogen chloride. Recrystallisation from ethyl acetate-methanol gave the title compound, mp. 117°–121° C. as a 56:44 mixture of diastereoisomers.

$^1$H-nmr δ(DMSO-$d_6$): 1.0–1.3 (3H, m); 2.68 (3H, d); 2.5–2.9 (1H, m); 3.0–3.7 (8H, complex m); 4.33 (2H, s); 4.5–4.9 (1H, m, exchanges with D$_2$O); 4.8–5.0 (1H, m); 6.92 (2H, d); 7.23 (2H, d); 7.3–7.8 (4H, m); 8.0–8.3 (1H, m, exchanges with D$_2$O); 8.9–9.4 (1H, brd m, exchanges with D$_2$O); 9.5–10.0 (1H, brd m, exchanges with D$_2$O).

EXAMPLE 4

N-[2-(4-(2-Hydroxyethoxy)phenyl)-1-methylethyl]-2-(2-hydroxyethoxy)-2-(3-chlorophenyl)ethanamine hydrochloride N-[2-(4-Carbomethoxymethoxyphenyl)-1-methylethyl]-2-(2-hydroxyethoxy)-2-(3-chlorophenyl)ethanamine (3.0 g) in dry tetrahydrofuran (30 ml) was added dropwise, with stirring, to a suspension of lithium aluminium hydride (1.0 g) in dry tetrahydrofuran (30 ml) and the resultant mixture heated under reflux for 3 hours. After cooling, water (1 ml), 10% aqueous sodium hydroxide (1 ml) and water (2 ml) were added carefully. Filtration and evaporation of the filtrate to dryness gave an oil which was converted to its hydrochloride salt by treatment with ethereal hydrogen chloride. Recrystallisation from ethyl acetate-methanoldiethyl ether gave the title compound, mp 86°–90° C. as a 49:51 mixture of diastereoisomers.

¹H-nmr δ(DMSO-d₆):

1.0–1.3 (3H, m); 2.6–2.9 (1H, m); 3.0–4.1 (12H, complex m); 4.7–4.9 (2H, m exchanges with D₂O); 4.9–5.2 (1H, m); 6.90 (2H, d); 7.23 (2H, d); 7.3–7.7 (4H, m); 8.8–9.4 (1H, brd m, exchanges with D₂O); 9.5–10.00 (1H, brd m, exchanges with D₂O).

EXAMPLE 5

N-[2-(4-(2-Methylaminoethoxy)phenyl)-1-methylethyl]-2-(2-hydroxyethoxy)-2-(3-chlorophenyl)ethanamine dihydrochloride hydrate To a stirred solution of N-[2-(4-(4-methylaminocarbonylmethoxyphenyl)-1-methylethyl]-2-(2-hydroxyethoxy)-2-(3-chlorophenyl)ethanamine (2.0 g) in dry tetrahydrofuran (25 ml) was added borane-dimethyl sulphide complex (6 ml), under nitrogen. The solution was heated under reflux for 3 hours, and after cooling to room temperature, methanol (20 ml) was added. This solution was allowed to stand ovenight at room temperature, heated under reflux for 1 hour, cooled, and hydrogen chloride gas passed through for 10 minutes. After dilution with diethyl ether, cooling to 0° C. and filtering the title compound was obtained as a 58:42 mixture of diastereoisomers, mp 204°–208° C.

¹H-nmr δ(DMSO-d₆+D₂O):

1.20 (3H, d); 2.70 (3H, s); 2.6–2.9 (1H, m); 3.0–3.8 (10H, complex m); 4.2–4.5 (2H, m); 4.7–5.1 (1H, m); 7.00 (2H, d); 7.29 (2H, d); 7.4–7.7 (4H, m).

EXAMPLE 6

N-[2-(4-Carbomethoxymethoxyphenyl)-1-methylethyl]-2-(2-hydroxyethoxy)-2-(3-trifluoromethylphenyl)ethanamine hydrochloride The title compound, m.p. 93°–97° C. (ethyl acetate-diethyl ether) was obtained, as a 66:34 mixture of diastereoisomers, from 1-(4-carbomethoxymethoxyphenyl)propan-2-one (4.40 g) and 2-(2-hydroxyethoxy)-2-(3-trifluoromethylphenyl)ethanamine (4.98 g) by an analogous procedure to that described in Example 1.

¹H nmr δ(DMSO-d₆):

1.0–1.4 (3H, m), 2.6–3.0 (1H, m), 3.10–4.0 (8H, m), 3.70 (3H, s), 4.80 (2H, s), 4.9–5.4 (2H, m, 1H exchanges with D₂O), 6.91 (2H, d), 7.23 (2H, d), 7.6–8.0 (4H, m), 9.0–9.6 (1H, m, exchanges with D₂O), 9.6–10.1 (1H, m, exchanges with D₂O).

EXAMPLE 7

N-[2-(4-Carbomethoxyphenyl)-1-methylethyl]-2-(2-hydroxyethoxy)-2-(3-chlorophenyl)ethanamine hydrochloride The title compound, m.p. 84°–87° C. (ethyl acetate-cyclohexane) was obtained, as a 65:35 mixture of diastereoisomers, from 1-(4-carbomethoxyphenyl)propan-2-one (3.57 g) and 2-(2-hydroxyethoxy)-2-(3-chlorophenyl)ethanamine (4.00 g) by an analogous procedure to that described in Example 1.

¹H nmr δ(DMSO-d₆):

1.0–1.3 (3H, m), 2.6–3.0 (1H, m), 3.0–3.8 (8H, m), 3.85 (3H, s), 4.0–4.5 (1H, m exchanges with D₂O), 4.96 (1H, t), 7.2–7.6 (6H, m), 7.91 (2H, d), 9.0–9.5 (1H, broad m, exchanges with D₂O), 9.6–10.1 (1H, broad m, exchanges with D₂O).

EXAMPLE 8

N-[2-(4-Carbomethoxymethoxyphenyl)-1-methylethyl]-2-(2-hydroxyethoxy)-2-phenylethanamine hydrochloride The title compound, m.p. 128°–132° C. (ethyl acetate-diethyl ether) was obtained as a 51:49 mixture of diastereoisomers from 1-(4-carbomethoxymethoxyphenyl)propan-2-one (4.40 g) and 2-(2-hydroxyethoxy)-2-phenylethanamine (3.62 g) by an analogous procedure to that described in Example 1.

¹H nmr δ(DMSO-d₆):

1.0–1.5 (3H, m), 2.6–3.0 (1H, m), 3.0–4.0 (8H, m), 3.70 (3H, s), 4.78 (2H, s), 4.7–5.2 (2H, m, 1H exchanges with D₂O), 6.92 (2H, d), 7.23 (2H, d), 7.3–7.6 (5H, m), 8.9–9.5 (1H, m, exchanges with D₂O), 9.6–10.3 (1H, m, exchanges with D₂O).

EXAMPLE 9

N-[2-(4-carbomethoxymethoxyphenyl)-1-methyl ethyl]-2-(2-hydroxyethoxy)-2-(2-benzofuranyl)ethanamine hydrochloride The title compound was prepared, as a 52:48 mixture of diastereoisomers, m.p. 125°–143° (ethyl acetate) from 1-(4-carbomethoxymethoxyphenyl)propan-2-one (1.7 g) and 2-(2-benzofuranyl)-2-(2-hydroxyethoxy)ethanamine (1.7 g) by an analogous procedure to that described in Example 1.

¹H nmr δ(DMSO-d₆):

1.16 (3H, m); 2.61–2.72 (1H, m); 3.28–3.55 (8H, m); 3.70 (3H, s); 4.77 (2H, s); 4.93 (1H, broad, exchanges with D₂O); 5.14–5.17 (1H, m); 6.88 (2H, d); 7.10 (1H, s); 7.18 (2H, d); 7.20–7.38 (2H, m); 7.61 (1H, d); 7.68 (1H, d); 9.09 (1H, broad, exchanges with D₂O); 9.66 (1H, broad, exchanges with D₂O).

EXAMPLE 10

N-[2-(4-Aminocarbonylmethoxyphenyl)-1-methylethyl]-2-(2-hydroxyethoxy)-2-(4-hydroxyphenyl)ethanamine N-[2-(4-Aminocarbonylmethoxyphenyl)-1-methylethyl]-2-(4-benzyloxyphenyl)-2-(2-hydroxyethoxy)ethanamine (3.5 g) in glacial acetic acid (30 ml) was hydrogenated in the presence of 10% Palladium on carbon at atmospheric pressure and room temperature until hydrogen uptake was complete. The solution was filtered through diatomaceous earth and the solvent removed under vacuum. The residue was partitioned between ethyl acetate and saturated aqueous sodium bicarbonate, the organic layer separated, dried (MgSO₄) and evaporated to give an oil. The oil was crystallised from ethyl acetate to give the title compound, m.p. 145°–160° C. as a 40:60 mixture of diastereoisomers.

¹H nmr δ(DMSO-d₆):

0.85 (3H, d); 2.2–2.95 (5H, m+2H, exchanges with D₂O); 2.95–3.55 (4H, m); 4.2 (1H, m); 4.35 (2H, s); 6.6–7.3 (8H, m+1H, exchanges with D₂O); 7.45 (2H, bd, exchanges with D₂O).

EXAMPLE 11

N-[2-(4-Carbomethoxymethoxyphenyl)-1-methylethyl]-2-(2-hydroxyethoxy)-2-(4-hydroxyphenyl)ethanamine hydrochloride The title compound was prepared as a 60:40 mixture of diastereoisomers, m.p. 138°–145° C. (ethylacetatemethanol) from N-[2-(4-carbomethoxymethoxyphenyl)-1-methylethyl]-2-(4-benzyloxyphenyl)-2-(2-hydroxyethoxy)ethanamine (5 g) by an analogous procedure to that described in Example 10.

$^1$H nmr δ(DMSO-d$_6$):
1.12 (3H, d); 2.6–2.7 (1H, m); 2.7–3.7 (8H, m+2H, exchanges with D$_2$O); 3.7 (3H, s); 4.5–4.8 (1H, m); 4.75 (2H, s); 6.68–7.05 (4H, m); 7.05–7.35 (4H, d); 8.5–10.2 (1H, bs, exchanges with D$_2$O); 9.65 (1H, bs, exchanges with D$_2$O).

EXAMPLE X 1

2-(3-Chlorophenyl)-1,3-dioxalane

A mixture of 3-chlorobenzaldehyde (30 g), ethylene glycol (20 ml) and 4-toluenesulphonic acid monohydrate in toluene (200 ml) was boiled under reflux for 5 h, the water formed during the reaction was removed with the aid of a Dean and Stark trap. The solvent was evaporated and the residue distilled under reduced pressure, 90°–100° C./0.2 mm to give the title compound as a colourless oil.

$^1$H-nmr δ(CDCl$_3$):
3.7–4.1 (4H, brd m); 5.67 (1H, brd s): 7.1–7.4 (3H, m); 7.45 (1H, s).

EXAMPLE X 2

1-(2-Hydroxyethoxy)-1-(3-chlorophenyl)acetonitrile

To a solution of 2-(3-chlorophenyl)-1,3-dioxolane (10 g) and zinc iodide (1 g) in dry diethyl ether (150 ml) was added dropwise with stirring trimethylsilyl cyanide (7 ml) in diethyl ether (10 ml). After 18 h at room temperature diethyl ether was added and the resultant solution washed with sodium carbonate solution, dried, filtered and evaporated to yield the title compound as an oil.

$^1$H-nmr δ(CDCl$_3$):
3.4–3.8 (5H, brd m); 5.28 (1H, s); 7.1–7.3 (3H, m); 7.40 (1H, s).

EXAMPLE X 3

2-(2-Hydroxyethoxy)-2-(3-chlorophenyl)ethanamine

A solution of 1-(2-hydroxyethoxy)-1-(3-chlorophenyl)acetonitrile (12 g) in dry diethyl ether (40 ml) was added dropwise with stirring to a mixture of lithium aluminium hydride (5 g) in dry diethyl ether (100 ml). After boiling under reflux for 3 h. the mixture was cooled and water (5 ml), 10% sodium hydroxide solution (5 ml) and water (10 ml) were added sequentially. The mixture was filtered and the filtrate washed twice with dichloromethane. The combined organic solutions were dried and evaporated to yield the title compound as an oil which was used without further purification.

$^1$H-nmr δ(CDCl$_3$):
3.86 (d, 2H); 3.0–3.4 (3H, m, exchanges with D$_2$O); 3.4–4.0 (4H, complex m); 4.31 (1H, t); 7.0–7.5 (4H, m).

EXAMPLE X 4

2-(3-Chlorophenyl)-1,3-dioxane

The title compound was prepared as a colourless oil, bp 95°–102° C./0.2 mm, from 3-chlorobenzaldehyde (24 g) and 1,3-propanediol (20 g) by an analogous procedure to that described in Example X 1.

$^1$H-nmr δ(CDCl$_3$):
1.33 (1H, m); 1.8–2.4 (1H, m); 3.84 (2H, m); 4.18 (2H, m); 5.40 (1H, s); 7.1–7.4 (3H, m); 7.49 (1H, s).

EXAMPLE X 5

1-(3-Hydroxypropoxy)-1-(3-chlorophenyl)acetonitrile

The title compound was prepared from 2-(3-chlorophenyl)-1,3-dioxane (10 g) and trimethylsilyl cyanide (7 ml) by an analogous procedure to that described in Example X 2 and was used without further purification in the next step.

EXAMPLE X 6

2-(3-Hydroxypropoxy)-2-(3-chlorophenyl)ethanamine

The title compound was prepared from 1-(3-hydroxypropoxy)-1-(3-chlorophenyl)acetonitrile (11 g) and lithium aluminium hydride (5 g) by an analogous procedure to that described in Example X 3.

$^1$H-nmr δ(CDCl$_3$):
1.5–1.8 (2H, m); 2.4–2.6 (3H, brd m exchanges with D$_2$O); 2.70 (2H, d); 3.1–3.5 (2H, m); 3.5–3.8 (2H, m); 4.09 (1H, t); 6.9–7.4 (4H, m).

EXAMPLE X 7

2-Phenyl-1,3-dioxalane

The title compound, b.p. 103°–105° C./2 mm was prepared from benzaldehyde and 1,2-dihydroxyethane as described in Example X 1.

EXAMPLE X 8

1-(2-Hydroxyethoxy)-1-phenylacetonitrile

The title compound was prepared from 2-phenyl-1,3-dioxalane (10 g) and trimethylsilyl cyanide (8.9 g) in the presence of zinc iodide as described in Example X 2, and was used without further purification.

EXAMPLE X 9

2-(2-Hydroxyethoxy)-2-phenylethanamine

The title compound was prepared from 1-(2-hydroxyethoxy)-1-phenylacetonitrile (10 g) and lithium aluminium hydride (4 g) as described in Example X 3.

$^1$H nmr δ(CDCl$_3$):
2.90 (2H, d), 3.08 (3H, broad s, exchanges with D$_2$O), 3.3–3.8 (4H, m), 4.33 (1H, t), 7.1–7.7 (5H, m).

EXAMPLE X 10

2-(3-Trifluoromethylphenyl)-1,3-dioxalane

The title compound, bp. 85°–90°/0.5 mm, was prepared from 3-trifluoromethylbenzaldehyde and 1,2-dihydroxyethane as described in Example X 1.

EXAMPLE X 11

1-(2-Hydroxyethoxy)-1-(3-trifluoromethylphenyl)acetonitrile

The title compound was prepared from 2-(3-trifluoromethylphenyl)-1,3-dioxalane and trimethylsilyl cyanide as described in Example X 2.

EXAMPLE X 12

2-(2-Hydroxyethoxy)-2-(3-trifluoromethylphenyl)ethanamine

The title compound was prepared from 1-(2-hydroxyethoxy)-1-(3-trifluoromethylphenyl)acetonitrile (12 g) and lithium aluminium hydride (4 g) as described in Example X 3.

$^1$H-nmr δ(CDCl$_3$):

2.86 (2H, d); 2.9–3.3 (3H, broad m, exchanges with D$_2$O); 3.4–3.9 (4H, complex m); 4.41 (1H, t); 7.2–7.8 (4H, complex m).

EXAMPLE X 13

2-(2-Benzofuranyl)-1,3-dioxalane

The title compound, bp. 100°–104°/0.3 mm was prepared from 2-formyl benzofuran and 1,2-dihydroxyethane as described in Example X 1.

$^1$H nmr δ(CDCl$_3$):

4.10 (4H, m); 6.10 (1H, s); 6.83 (1H, s); 7.15–7.65 (4H, m).

EXAMPLE X 14

2-(2-Benzofuranyl)-2-(2-hydroxyethoxy)ethanamine

To a solution of 2-(2-benzofuranyl)-1,3-dioxalane (21.38 g) and zinc iodide (0.5 g) in dry diethyl ether (200 ml) was added, dropwise, with stirring, trimethylsilylcyanide (15 ml). After 18 hours at room temperature, the solution was added dropwise, with stirring, to a mixture of lithium aluminium hydride (5 g) in dry diethyl ether (200 ml). After boiling under reflux for 3 hours the mixture was cooled and water (5 ml), 10% NaOH solution (5 ml) and water (15 ml) were added sequentially. The mixture was diluted with dichloromethane (50 ml) and filtered. The filtrate was dried and evaporated to an oil which was purified by column chromatography on silica gel. Elution with acetonitrile:methanol:ammonium hydroxide (15:2:1) gave the title compound as an oil.

$^1$H nmr δ(CDCl$_3$):

3.20 (2H, d); 3.45–4.0 (m, 4H+3H, exchanges with D$_2$O); 4.55 (1H, t); 6.65 (1H, s); 7.0–7.60 (4H, m).

EXAMPLE X 16

2-(4-Benzyloxyphenyl)-2-(2-hydroxyethoxy)ethanamine

The title compound was prepared as a yellow solid from 2-(4-benzyloxyphenyl)-1,3-dioxalane as described in Example X 14.

$^1$H nmr δ(CDCl$_3$):

2.4 (3H, bs, exchanges from D$_2$O); 2.87 (2H, d); 3.3–3.9 (4H, m); 4.28 (1H, t); 5.05 (2H, s); 6.8–7.6 (9H, m).

EXAMPLE X 15

2-(4-Benzyloxyphenyl)-1,3-dioxalane

The title compound was prepared as an oil, which crystallised on standing, from 4-benzyloxybenzaldehyde and 1,2-dihydroxyethane as described in Example X 1.

$^1$H nmr δ(CDCl$_3$):

3.8–4.2 (4H, broad m); 5.0 (2H, s); 5.7 (1H, s); 6.9 (2H, d); 7.2–7.7 (7H, m).

EXAMPLE X 17

N-[2-(4-Carbomethoxymethoxyphenyl)-1-methylethyl]-2-(4-benzyloxyphenyl)-2-(2-hydroxyethoxy)ethanamine The title compound was prepared as an oil from 1-(4-carbomethoxymethoxyphenyl)propan-2-one (4.52 g) and 2-(4-benzyloxyphenyl)-2-(2-hydroxyethoxy)ethanamine (5.84 g) as described in Example 1.

$^1$H nmr δ(CDCl$_3$):

1.05 (3H, d); 2.5–3.1 (7H, m); 3.3–3.7 (4H, m); 3.8 (3H, s); 4.4 (1H, m); 4.6 (2H, s); 5.0 (2H, s); 6.65–7.55 (13H, m).

EXAMPLE x 18

N-[2-(4-Aminocarbonylmethoxyphenyl)-1-methylethyl]-2-(4-benzyloxyphenyl)-2-(2-hydroxyethoxy)ethanamine Ammonia gas was bubbled through an ice cooled solution of N-[2-(4-carbomethoxymethoxyphenyl)-1-methylethyl]-2-(4-benzyloxyphenyl)-2-(2-hydroxyethoxy)ethanamine (4.2 g) in methanol (50 ml) for 10 mins. The resulting solution was allowed to remain at room temperature overnight, after which time the solvent was evaporated to give a white solid (3.5 g).

$^1$H nmr δ(DMSO-d$_6$):

0.95 (3H, d); 2.3–3.0 (5H, m); 3.3–3.7 (4H, m); 3.9 (2H, bs, exchanges with D$_2$O); 4.15–4.5 (2H, s+1H, m); 5.10 (2H, s); 6.75–7.75 (13H, m+2H, exchanges with D$_2$O).

DEMONSTRATION OF EFFECTIVENESS OF COMPOUNDS (a) Anti-hyperglycaemic activity

Female CFLP mice, weighing approximately 25 g, were fasted for 24 hours prior to the study. The compounds under study were administered orally as an aqueous solution to each of 6 mice. 30 minutes later a blood sample (10 μl) was obtained from the tail for the analysis of blood glucose. Immediately after taking this blood sample, glucose (1 g/Kg body weight) was administered subcutaneously to each mouse. 6 mice were given water as a control. Blood samples were then obtained from each mouse at 30 minute intervals for 120 minutes.

Compounds that produced a significant (P<0.05) reduction of blood glucose, compared with control mice given water, at any time interval, were considered active. The area under the blood glucose curve over the 2 hour period after the administration of the glucose was calculated for each compound and compared with the value for control animals.

| Compounds of Example No. | Dose (μmol/Kg) | % Reduction in area under Blood Glucose Curve |
|---|---|---|
| 1 | 2.5 | 53 |
| 3 | 2.5 | 41 |
| 4 | 2.5 | 38 |
| 5 | 25.0 | 31 |
| 6 | 2.5 | 21 |
| 7 | 25.0 | 36 |
| 8 | 25.0 | 36 |
| 10 | 25.0 | 19 |
| 11 | 25.0 | 39 |

(b) Effect on Energy Expenditure

The effect of the compounds on the energy expenditure of mice was demonstrated by means of the following procedure:

Female CFLP mice, each weighing approximately 24 g was given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 3 hours after dosing from the volume of air leaving the boxes and its oxygen content, following the principles described by J. B. de V. Weir, *J. Physiol.* (London), 109, 1-9 (1949).

| Compounds of Example No. | Dose mg/kg po | Mean Energy Expenditure (0-3 h) |
|---|---|---|
| 1 | 22.9 | 147 |
| 2 | 23.6 | 170 |
| 3 | 22.8 | 167 |
| 4 | 21.5 | 158 |
| 5 | 24.9 | 121 |
| 6 | 24.6 | 113 |
| 7 | 21.4 | 134 |
| 8 | 21.2 | 159 |
| 9 | 23.2 | 125 |

Toxicity

No toxic effects were observed in the above tests.
We claim:

1. A compound of formula (I):

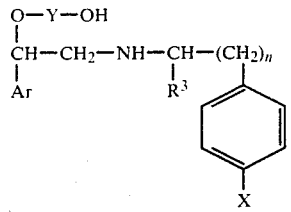

or a pharmaceutically acceptable salt thereof, wherein:
Ar is benzofuran-2-yl, or phenyl optionally substituted by groups $R^1$ and/or $R^2$ wherein $R^1$ is halogen, trifluoromethyl or hydroxy and $R^2$ is halogen;
$R_3$ is hydrogen or methyl;
X is $-O(CH_2)_2CO_2H$ or $-CO_2H$ or a pharmaceutically acceptable ester or amide thereof, or $O(CH_2)_bM$ in which
a is an integer from 1 to 6,
b is an integer from 2 to 7,
M is hydroxy, $C_{1-6}$ alkoxy, phenyl $C_{1-6}$ alkoxy, or $-NR^4R^5$ in which $R^4$ and $R^5$ are each hydrogen or $C_{1-6}$ alkyl or together form a five or six membered heterocyclic ring;
Y is $C_{2-6}$ straight or branched alkylene, with at least two carbon atoms between the —O— and —OH; and
n is 1 or 2.

2. A compound according to claim 1 wherein Ar is phenyl substituted by $R^1$ is halogen in the meta- (or 3-) position on the phenyl ring.

3. A compound according to claim 2 wherein $R^1$ is chlorine.

4. A compound according to claim 1 wherein $R^3$ is methyl.

5. A compound according to claim 1 wherein a is 1 and b is 2.

6. A compound according to claim 1 wherein n is 1.

7. A compound according to claim 1 wherein Y is ethylene or n-propylene.

8. A compound selected from the group consisting of N-[2-(4-Carbomethoxymethoxyphenyl)-1-methylethyl]-2-(2-hydroxyethoxy)-2-(3-chlorophenyl)ethanamine,
N-[2-(4-carbomethoxymethoxyphenyl)-1-methylethyl]-2-(3-hydroxypropoxy)-2-(3-chlorophenyl)ethanamine,
N-[2-(4-methylaminocarbonylmethoxyphenyl)-1-methylethyl]-2-(2-hydroxyethoxy)-2-(3-chlorophenyl)ethanamine,
N-[2-(4-(2-hydroxyethoxy)phenyl)-1-methylethyl]-2-(2-hydroxyethoxy)-2(3-chlorophenyl)ethanamine,
N-[2-(4-(2-methylaminoethoxy)phenyl)-1-methylethyl]-2-(2-hydroxyethoxy)-2-(3-chlorophenyl)ethanamine,
N-[2-(4-carbomethoxymethoxyphenyl)-1-methylethyl]-2-(2-hydroxyethoxy)-2-(3-trifluoromethylphenyl)ethanamine,
N-[2-(4-carbomethoxyphenyl)-1-methylethyl]-2-(2-hydroxyethoxy)-2-(3-chlorophenyl)ethanamine,
N-[2-(4-carbomethoxymethoxyphenyl)-1-methylethyl]-2-(2-hydroxyethoxy)-2-phenylethanamine,
N-[2-(4-carbomethoxymethoxyphenyl)-1-methylethyl-2-(2-hydroxyethoxy)-2-(2-benzofuranyl)ethanamine,
N-[2-(4-aminocarbonylmethoxyphenyl)-1-methylethyl]-2-(2-hydroxyethoxy)-2-(4-hydroxyphenyl)ethanamine,
N-[2-(4-carbomethoxymethoxyphenyl)-1-methylethyl]-2-(2-hydroxyethoxy)-2-(4-hydroxyphenyl)ethanamine,
or a pharmaceutically acceptable salt thereof.

9. A pharmaceutical composition for the treatment and/or prophylaxis of obesity and/or hyperglycaemia comprising an effective amount of compound according to claim 1 together with a pharmaceutically acceptable carrier.

10. A method of treatment and/or prophylaxis of obesity and/or hyperglycaemia in mammals including humans which method comprises administering an effective, non-toxic amount of a compound according to claim 1, to the mammal.

11. N-[2-(4-carbomethoxymethoxyphenyl)-1-methylethyl]-2-(2-hydroxyethoxy)-2-(3-chlorophenyl)ethanamine or a pharmaceutically acceptable salt thereof.

12. A pharmaceutical composition for the treatment and/or prophylaxis of obesity and/or hyperglycaemia comprising an effective amount of N-[2-(4-carbomethoxymethoxyphenyl)-1-methylethyl]-2-(2-hydroxyethoxy)-2-(3-chlorophenyl)ethanamine or a pharmaceutically acceptable salt thereof with a pharmaceutically acceptable carrier.

13. A method of treatment and/or prophylaxis of obesity and/or hyperglycaemia in mammals which method comprises administering an effective, non-toxic amount of N-[2-(4-carbomethoxymethoxyphenyl)-1-methylethyl]-2-(2-hydroxyethoxy)-2-(3-chlorophenyl)ethanamine or a pharmaceutically acceptable salt thereof to said mammal.

* * * * *

UNITED STATES PATENT AND TRADEMARK OFFICE
CERTIFICATE OF CORRECTION

PATENT NO. : 4,692,465

DATED : September 8, 1987

INVENTOR(S) : Richard M. Hindley, John Berge

It is certified that error appears in the above-identified patent and that said Letters Patent is hereby corrected as shown below:

Claim 1, line 39, that portion of the formula reading "X is $-O(CH_2)_2CO_2H$" should read -- X is $-O(CH_2)_aCO_2H$ --.

Claim 2, line 2, that portion of the formula reading "$R_1$ is halogen" should read -- $R_1$ which is halogen.

Signed and Sealed this

Ninth Day of August, 1988

*Attest:*

DONALD J. QUIGG

*Attesting Officer*     *Commissioner of Patents and Trademarks*